United States Patent [19]

Rucki

[11] Patent Number: 5,679,052
[45] Date of Patent: Oct. 21, 1997

[54] ADJUSTABLE BREAST PACK

[76] Inventor: Lawrence A. Rucki, 51 Middlesex St., North Chelmsford, Mass. 01863

[21] Appl. No.: 501,631

[22] Filed: Jul. 12, 1995

[51] Int. Cl.$^6$ ............................... A61F 7/00; A41B 3/00
[52] U.S. Cl. ................... 450/57; 2/267; 607/96; 607/108; 450/38
[58] Field of Search .................... 2/73, 267, 268, 2/243.1; 450/53, 54, 55, 56, 57, 30, 31, 32, 36, 38; 602/26, 13; 607/96, 108, 109, 110

[56] References Cited

U.S. PATENT DOCUMENTS

| | | | |
|---|---|---|---|
| D. 365,399 | 12/1995 | Silver | D24/206 |
| 2,298,361 | 10/1942 | Freund | 607/108 |
| 5,304,215 | 4/1994 | MacWhinnie et al. | 607/108 |
| 5,441,534 | 8/1995 | MacWinnie et al. | 607/108 |
| 5,476,490 | 12/1995 | Silver | 607/108 |
| 5,527,268 | 6/1996 | Gildersleeve et al. | 602/26 |
| 5,534,020 | 7/1996 | Cheney, III et al. | 607/108 |

FOREIGN PATENT DOCUMENTS 821150   11/1937   France .................. 607/109

Primary Examiner—Jeanette E. Chapman
Attorney, Agent, or Firm—William Nitkin

[57] ABSTRACT

A breast pack for providing warm or cold therapy to the female breast is disclosed. The breast pack can be formed of a generally C-shaped or semicircular top layer and bottom layer, each having a central opening, which layers are joined along their perimeter edges to define a pocket therebetween which is filled with a thermal gel material. The breast pack, when heated or cooled, retains such heat or coolness for a long period of time. In use, the breast pack is formed into a conical shape by overlapping its ends and adjusted to the size and contour of the user's breast. The breast pack can be retained in position within the user's bra. A central opening in the C-shaped breast pack accommodates the nipple area of the user's breast.

3 Claims, 2 Drawing Sheets

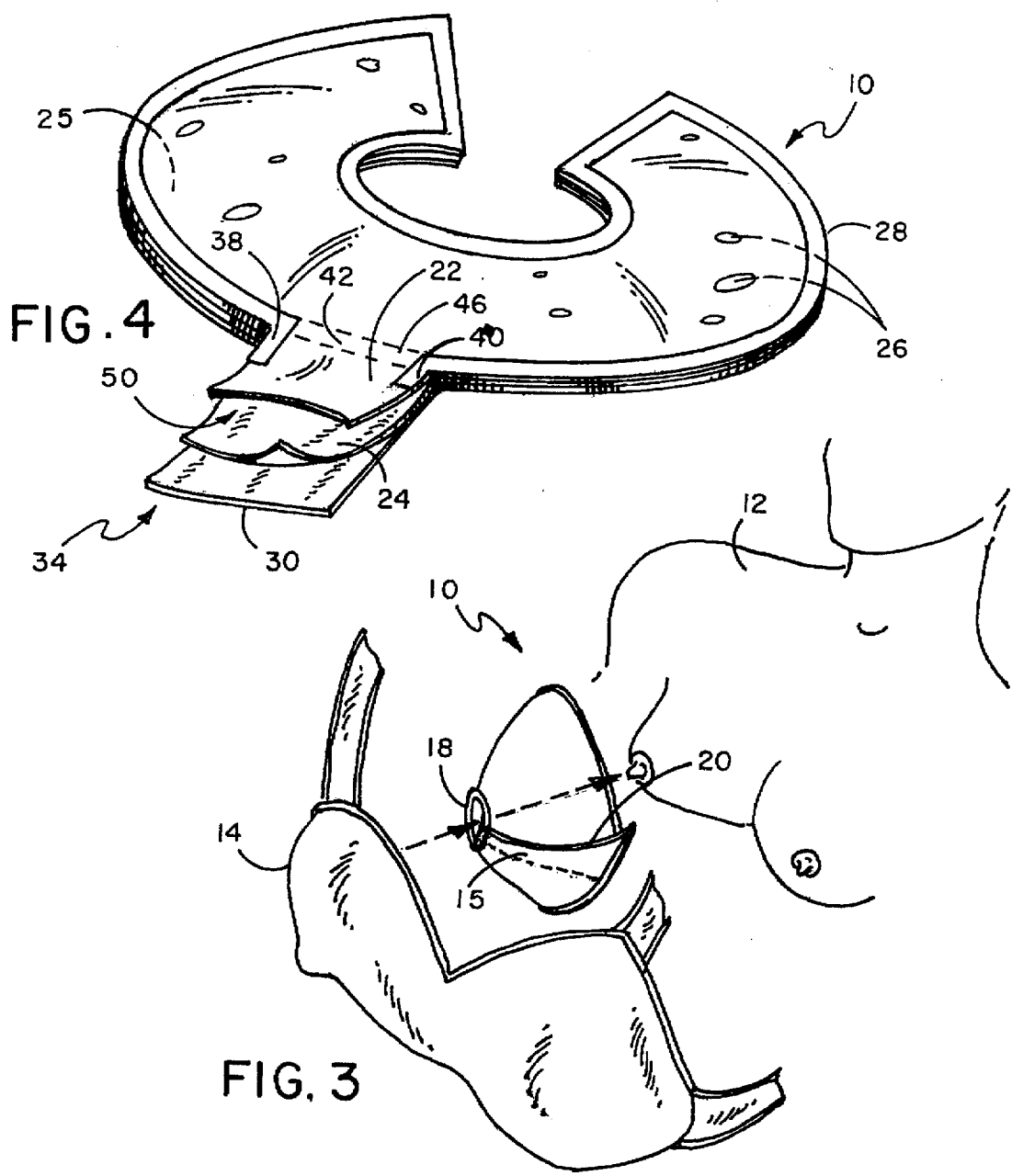

ADJUSTABLE BREAST PACK

BACKGROUND OF THE INVENTION

1. Field of the Invention

The present invention resides in the area of breast packs and more particularly relates to a breast pack that can be heated or cooled to provide therapy to women experiencing breast discomfort.

2. Description of the Prior Art

Many women suffer the discomfort of swelling and tenderness of the breasts due to lactation during postpartum nursing. Cold therapy to reduce swelling is recommended for women who are not breastfeeding while a warm therapy is recommended for nursing mothers.

A number of thermal packs are known in the prior art. U.S. Pat. No. Re 14,024 to Whitmarsh and U.S. Pat. No. 5,050,595 to Krafft disclose cup-shaped thermal packs which can be applied to the breasts. These prior art devices are generally not adjustable for various sizes of breasts. U.S. Pat. No. 5,133,348 issued to Mayn discloses a contoured cooling pack which can be applied to the breast. This device, however, does not provide a central opening for the nipple area of the breast to prevent cooling of the nipple, does not contour well nor conveniently fit the breast and would be difficult, if not impossible to wear beneath a bra. U.S. Pat. No. 5,304,215 to MacWhinnie et al discloses a cylindrical, disk-shaped, thermal heat pack having radially extending segments separated by tapered apertures to conform to various sized female breasts. The MacWhinnie device, though, does not provide a central opening for the nipple area and is difficult to use due to the necessity of aligning its segments. German publication DE 004141806 A of Mueller discloses several devices consisting of thermal bags of various shapes and designs, some being similar to those of MacWhinnie, including triangles, droplets and parallelograms. Such devices would require several bags in order to surround the entire breast area.

SUMMARY OF THE INVENTION

It is an object of the breast pack of this invention to overcome the disadvantages of the prior art by providing a simple, flexible pack which device can be adjusted for various breast sizes. The generally C-shaped flexible design is capable of being formed into an open-topped, truncated, conical shape by the user to conform to the size and contours of the user's breast.

It is a further object of this invention to provide an adjustable pack capable of being heated or cooled.

It is a still further object of this invention to prevent discomfort to the sensitive nipple area of the breast by providing a central opening while providing therapy to the entire remaining portion of the breast.

To accomplish the objects of this invention, flexible and generally C-shaped or semi-circular top and bottom layers are fastened together by a seam to form a pocket with a gel material capable of being heated or cooled filling such pocket thus created. The term "C-shaped" is used herein to include semi-circular configurations. A flexible lining of soft material can be attached to the outer surface of the bottom layer to prevent discomfort to the skin which is adjacent thereto when the device is in use. The end portions of the C-shaped top and bottom layers containing the gel material are overlapped when in use to form a conical shape which can be size-adjusted by such overlapping to fit all sizes of breasts. The conical shape of the device also defines a central opening in the breast pack to accommodate the nipple area of the user's breast. The stiffness of the gel helps to hold the breast pack in its overlapped, conical configuration so that it is easy to position on the breast. The consistency of the gel is such that it remains in place without settling to the bottom of the breast pack when worn.

BRIEF DESCRIPTION OF THE DRAWINGS

FIG. 3 illustrates a perspective view of the breast pack of this invention with its ends overlapping for application to a user's breast.

FIG. 4 illustrates a perspective view of the breast pack of this invention before the tongue is removed.

DESCRIPTION OF THE PREFERRED EMBODIMENT(S)

Figure 1:
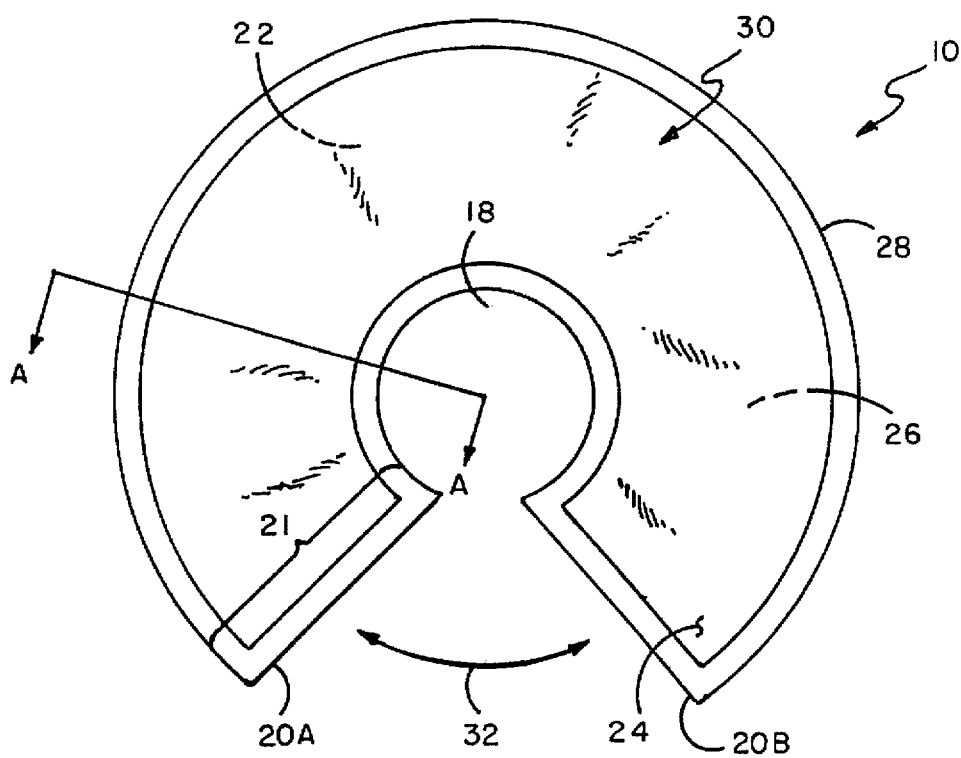
FIG. 1 illustrates a bottom plan view of the C-shaped breast pack of this invention.
Figure 2:
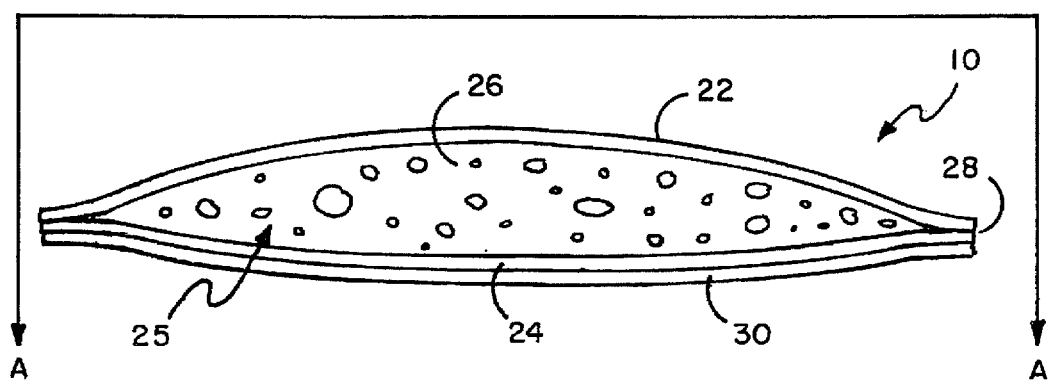
FIG. 2 illustrates a cross-sectional view taken along line A—A of FIG. 1.

FIG. 1 illustrates a bottom plan view of breast pack 10 of this invention showing the general configuration of the preferred embodiment. Breast pack 10 has top layer 22, bottom layer 24, seam 28 and thermal material 26 disposed between top layer 22 and bottom layer 24. Top and bottom layers 22 and 24 are flat and generally C-shaped layers having a width 21 of generally several inches with an open area 32 defined between first and second ends 20A and 20B. The continuous top and bottom layers can be generally C-shaped or semi-circular in shape. The material used for the top and bottom layers must be flexible, such as plastic films. For both the top and bottom layers 22 and 24 a plastic film of polyethylene with an ethyl vinyl acetate (EVA) additive of 18% is preferred. EVA is tolerant to cold temperatures and will prevent the polyethylene from cracking due to cool temperatures. Seam 28, formed by heat-sealing, fastens the top and bottom layers 22 and 24 together. Pocket 25, as seen in FIG. 2, is formed when top and bottom layers 22 and 24 are sealed along seam 28. Pocket 25 is substantially filled with a thermal gel material 26 which is evenly distributed throughout the pocket. The sealed-together top layer 22 and bottom layer 24 define a central opening 18 for accommodating the nipple area of the female breast when breast pack 10 is in use. The generally circular central opening 18 requires a minimum radius of approximately 3 cm to prevent cooling of the nipple area when ends 20A and 20B are overlapped when the device is in use.

FIG. 2 shows a cross-sectional view of breast pack 10 taken along line A—A of FIG. 1. Disposed within pocket 25 is thermal gel material 26 which can be a well-known compound such as propylene glycol gel which is capable of being heated or cooled, retaining the heat of cold for a long period of time. When cooled, propylene glycol gel will remain cold for about 1 hour.

As shown in FIG. 2, flexible lining 30, which can be a non-woven fabric lining such as non-woven polypropylene material, is positioned covering the outer surface of bottom layer 24. Flexible lining 30 prevents discomfort from too much heat or cold being directly applied to the breast during use of breast pack 10 and is softer and more comfortable against the skin than the plastic layer alone would be. Lining 30 can be heat-sealed around its edges along with top and bottom layers 22 and 24 when creating seam 28. Flexible lining 30 can be of the same generally C-shaped or semi-circular shape as bottom layer 24 and have a central opening similar in shape and size to central opening 18.

FIG. 3 illustrates a perspective view of breast pack 10 of this invention about to be applied to a breast of user 12. First and second ends 20A and 20B of breast pack 10, as seen in FIG. 1, are overlapped when in use to form an open-ended, truncated, conical shape which can be size-adjusted by the amount of overlap 15 to conform to the size and shape of the user's breast. Central opening 18 aligns to fit over the nipple area 16 of user 12. Adjustable breast pack 10 can be held in place by bra 14.

FIG. 4 illustrates a perspective view of breast pack 10 during manufacture showing tongue 34 through which thermal gel material 26 can be entered into pocket 25, as seen in FIG. 2. Tongue 34 can be formed of similar shaped extensions of the bottom layer, top layer and lining.

During manufacture several breast packs can be arranged on stacked layers of large sheets of top layer material, bottom layer material and lining material. Each breast pack 10 is heat-sealed around its C-shaped perimeter and also along sides 38 and 40 of tongue 34 to form an entrance 50 between top and bottom layers 22 and 24 for entry of thermal gel material 26. Each pack is then diecut cold around its edges, leaving tongue 34 attached. Pocket 25 is filled with approximately 10–11 oz of propylene gel 26. Once thermal gel material 26 has been entered through entrance 50 in tongue 34, seal area 42 is closed by heat-sealing, and tongue 34 is then cut off outside seal area 42 along line 46.

Although the present invention has been described with reference to particular embodiments, it will be apparent to those skilled in the art that variations and modifications can be substituted therefor without departing from the principles and spirit of the invention.

I claim:

1. A breast pack capable of conforming to the contours of the female breast when in use, comprising:

a generally C-shaped, flexible top layer made of a thin plastic film of polyethylene with an ethyl vinyl acetate additive of 18% having first and second ends, said top layer having a perimeter edge;

a generally C-shaped, flexible bottom layer made of a thin plastic film of polyethylene with an ethyl vinyl acetate additive of 18% having first and second ends, said bottom layer having a perimeter edge and an outer surface;

a seam fastening said top and bottom layers together along said perimeter edges of said top and bottom layers, defining a pocket therebetween;

propyleneglycol thermal gel material of a consistency stiff enough to remain in place without settling disposed within said pocket;

a central opening having a minimum radius of approximately 3 cm defined within said sealed top and bottom layers for accommodating the nipple area of said female breast when said breast pack is in use with said first and second ends overlapping to form an adjustable, open-ended, truncated conical shape when positioning said breast pack against the breast; and a flexible lining of non-woven polypropylene material of similar size and shape to said bottom layer positioned adjacent to said outer surface of said bottom layer and affixed thereto by said seam.

2. The breast pack of claim 1 wherein said central opening has a radius of approximately 3 cm.

3. The breast pack of claim 1 wherein said seam is formed by heat-sealing means.

* * * * *